United States Patent [19]
Au-Young et al.

[11] Patent Number: 5,972,649
[45] Date of Patent: Oct. 26, 1999

[54] POLYNUCLEOTIDE SEQUENCE ENCODING HUMAN MULTIPLE ENDOCRINE NEOPLASIA TYPE 1 PROTEIN

[75] Inventors: Janice Au-Young, Berkeley; Peter A. Covitz, San Francisco; Y. Tom Tang, Sunnyvale; Lynn E. Murry, Portola Valley, all of Calif.

[73] Assignee: Incyte Pharmaceuticals, Inc., Palo Alto, Calif.

[21] Appl. No.: 08/865,337

[22] Filed: May 29, 1997

[51] Int. Cl.$^6$ .......................... C12N 15/11; C12N 15/63; C12N 1/21; C12N 15/00
[52] U.S. Cl. ................... 435/69.1; 536/23.1; 435/252.3; 435/320.1
[58] Field of Search ..................... 536/23.1; 435/320.1, 435/252.3, 69.1

[56] References Cited

U.S. PATENT DOCUMENTS 4,889,806 12/1989 Olson et al. .......................... 435/172.3

OTHER PUBLICATIONS

Hillier et al (Genbank Acession # H16350, NIDg881170), 1995.
Sambrook et al (Molecular Cloning, A Lab. Manual, 2nd Edition, Cold Spring Harbor Press, Cold Spring Harbor, 1989.
Burgess et al (J. Cell Bio, 111: 2129–2138), 1990.
Lazar et al (Mol & Cell Bio, 8: 1247–1252), 1988.
Tao et al (J. Immunol, 143: 2595–2601), 1989.
Hillier et al (Genbank Acession # H14300, NIPg879120), 1995.
Emmert–Buck, M.R. et al., "Laser capture microdissection." *Science* (1996) 274:998–1001.
Chandrasekharappa, S. C. et al., "Positional Cloning of the Gene for Multiple Endocrine Neoplasia–Type 1." *Science*(1997) 276:404–407. (GI 1945387).
Chandrasekharappa, S.C. et al. (GI 1945386), GenBank Sequence Database (Accession U93236), National Center for Biotechnology Information, National Library of Medicine, Bethesda, Maryland, 20894.

*Primary Examiner*—Lila Feisee
*Assistant Examiner*—Susan Ungar
*Attorney, Agent, or Firm*—Incyte Pharmaceuticals, Inc.

[57] ABSTRACT

The invention provides a human multiple endocrine neoplasia type 1 protein (MEND1) and polynucleotides which identify and encode MEND1. The invention also provides expression vectors, host cells, agonists, antibodies and antagonists. The invention also provides methods for treating disorders associated with expression of MEND1.

9 Claims, 10 Drawing Sheets

```
5' nAN GCG TGC GCC GTG CCT AGT GTG GGA TGC CGC CGC CCA CCC GCC         54
GCC ATG GGG CTG AAG GCC GCC CAG AAG ACG CTG TTC CCG CTG GAG GAG CCC   108
     M   G   L   K   A   A   Q   K   T   L   F   P   L   E   E   P
    63              72              81              90              99
GAC GTG GTG CGC CTG TTT GCT GCC CTG GGC CGA GAG CAT CTG GCT CGC GTG  162
 D   V   V   R   L   F   A   A   L   G   R   E   H   L   A   R   V
   117             126             135             144             153
CTC CTT TCC TTG GTG CTG GGC TTC GTG GAG TTC CAG ACC TTT GTC AAC CGC  216
 L   L   S   L   V   L   G   F   V   E   F   Q   T   F   V   N   R
   171             180             189             198             207
ATC CCT ACC AAC GTT CCC GAG CTC ACC CGT TAT AGC AGC GAT GGG ACT GTC  270
 I   P   T   N   V   P   E   L   T   R   Y   S   S   D   G   T   V
   225             234             243             252             261
CCT GGC GGC CTC ACC TAC TTT CCC CAG ATC GCC TTT CCT CTC AGT CCT ATA  324
 P   G   G   L   T   Y   F   P   Q   I   A   F   P   L   S   P   I
   279             288             297             306             315
TAT GCC CGC TTC ACC GCC TCC AGC CGT GAG CTG GTG AAG AAG GTC TCC CTC  378
 Y   A   R   F   T   A   S   S   R   E   L   V   K   K   V   S   L
   333             342             351             360             369
CGA GAA GGG GGT GTC TCC AGC CGT GAG CTG GTG AAG GAT GCC CAC ATC CAG  432
 R   E   G   G   V   S   S   R   E   L   V   K   D   X   H   I   Q
   387             396             405             414             423
TGG AAC AGC CTC AGC CGC TCC TAC TTC AAG GAT GTC TCC ATC CAG TCC CTC  486
 W   N   S   L   S   R   S   Y   F   K   D   V   S   I   Q   S   L
   441             450             459             468             477
```

FIGURE 1A

|     | 495 | 504 | 513 | 522 | 531 | 540 |
|-----|-----|-----|-----|-----|-----|-----|
| TTC | AGC | ATC | ACA | ACC | AAA | TTG | GAC | TCC | GGN | GTG | GCC | TTT | GCT | GTG | NNT |
| F   | S   | I   | T   | T   | K   | L   | D   | S   | G   | V   | A   | F   | A   | V   | X   |
|     | 549 | 558 | 567 | 576 | 585 | 594 |
| GGG | CCC | AAT | GGG | GAG | CAG | ACA | GCT | GAG | GTC | ACC | TGG | CAC | GGC | AAG | GGC | AAC | GAG |
| G   | P   | N   | G   | E   | Q   | T   | A   | E   | V   | T   | W   | H   | G   | K   | G   | N   | E   |
|     | 603 | 612 | 621 | 630 | 639 | 648 |
| GAC | CGC | AGG | GGC | CAG | ACA | GTC | AAT | GCC | GGT | GTG | GCT | GAG | GTG | AGC | TGG | CTG | TAC |
| D   | R   | R   | G   | Q   | T   | V   | N   | A   | G   | V   | A   | E   | V   | S   | W   | L   | Y   |
|     | 657 | 666 | 675 | 684 | 693 | 702 |
| CTG | AAA | GGA | TCA | TAC | ATG | CGC | TGT | GAC | ATT | GAC | CGC | AAG | ATG | GAG | GCG | TTC | ATG | GTG |
| L   | K   | G   | S   | Y   | M   | R   | C   | D   | I   | D   | R   | K   | M   | E   | A   | F   | M   | V   |
|     | 711 | 720 | 729 | 738 | 747 | 756 |
| TGT | GCC | ATC | AAC | CCT | ATT | TCC | ATT | GAC | CTG | CAC | ACC | TCG | CTG | GAG | CTT | CTG | CAG |
| C   | A   | I   | N   | P   | I   | S   | I   | D   | L   | H   | T   | S   | L   | E   | L   | L   | Q   |
|     | 765 | 774 | 783 | 792 | 801 | 810 |
| CTG | CAG | AAG | CTG | CTC | TGG | CTC | TAT | GAC | CTG | GGA | CAT | CTG | GAG | GAG | CTT | GAA | AGG | TAC |
| L   | Q   | K   | L   | L   | W   | L   | Y   | D   | L   | G   | H   | L   | E   | E   | L   | E   | R   | Y   |
|     | 819 | 828 | 837 | 846 | 855 | 864 |
| CCC | ATG | GCC | TTA | GGG | AAC | CTG | GCA | GAT | CTA | GAG | GAG | CTG | GAG | CCC | ACC | CCT | GGC |
| P   | M   | A   | L   | G   | N   | L   | A   | D   | L   | E   | E   | L   | E   | P   | T   | P   | G   |
|     | 873 | 882 | 891 | 900 | 909 | 918 |
| CGG | CCA | GAC | CCS | RGG | GCG | CTG | CTR | CAC | AAG | GGC | ATT | GCT | TCA | GCC | AAG | ACC | TAC |
| R   | P   | D   | P   | X   | A   | L   | L   | H   | K   | G   | I   | A   | S   | A   | K   | T   | Y   |

```
     927              936              945              954              963              972
TAT  CGG  GAT  GAA  CAC  ATC  TAC  CCC  TAC  ATG  TAC  CTG  GCT  TAC  CAC  TGT  CGC
 Y    R    D    E    H    I    Y    P    Y    M    Y    L    A    Y    H    C    R
     981              990              999             1008             1017             1026
AAC  CGC  AAT  GTG  CGG  GAA  SCC  CTG  CAG  GCC  CTR  GGC  AGA  GAC  ACG  GCC  ACT  CTC
 N    R    N    V    R    E    X    L    Q    A    L    G    R    D    T    A    T    L
    1035             1044             1053             1062             1071             1080
ATC  CAG  GAC  TAC  AAC  TAC  TGC  CGG  GAA  GAC  GAG  GAG  ATC  TAC  AAG  GAG  TTC  TTT
 I    Q    D    Y    N    Y    C    R    E    D    E    E    I    Y    K    E    F    F
    1089             1098             1107             1116             1125             1134
GAA  GTA  GCC  AAT  GAT  GTC  ATC  CCC  AAC  CTG  CTG  AAG  GAG  GCA  GCC  AGC  TTG  CTG
 E    V    A    N    D    V    I    P    N    L    L    K    E    A    A    S    L    L
    1143             1152             1161             1170             1179             1188
GAG  GCG  GGC  GAG  GAG  CCG  GGG  GAG  CAA  AGC  CAG  GGC  ACC  CAG  AGC  CAA  GGT
 E    A    G    E    E    P    G    E    Q    S    Q    G    T    Q    S    Q    G
    1197             1206             1215             1224             1233             1242
TCC  GCC  CTC  CAG  GAC  CCT  GAG  TGC  TTC  GCC  CAC  CTG  CTG  CGA  TTC  TAC  GAC  GGC
 S    A    L    Q    D    P    E    C    F    A    H    L    L    R    F    Y    D    G
    1251             1260             1269             1278             1287             1296
ATC  TGC  AAA  TGG  GAG  GAG  GGC  AGT  CCC  ACG  CCT  GTG  CTG  CAC  GTG  GGC  TGG  GCA
 I    C    K    W    E    E    G    S    P    T    P    V    L    H    V    G    W    A
    1305             1314             1323             1332             1341             1350
CCT  TTC  TTG  TNG  CAG  TCC  CTA  NGC  CGT  TTT  GAN  GGA  CAG  GTG  CNG  CAG  AAG  GTG
 P    F    L    X    Q    S    L    X    R    F    X    G    Q    V    X    Q    K    V
```

```
      1359            1368            1377            1386            1395            1404
CGC ATA GTG ANC CGA GAT GCC GAG GCT GCC GAG NCC AAG CCA GAG GAG CCC CCG
 R   I   V   X   R   D   A   E   A   A   E   X   K   P   E   E   P   P
      1413            1422            1431            1440            1449            1458
CCG CCC AAG AAG CCA GCA CTG GAC AAG GGC CTG GGC ACC GGC CAG GGC GCA GTG
 P   P   K   K   P   A   L   D   K   G   L   G   T   G   Q   G   A   V
      1467            1476            1485            1494            1503            1512
TCA GGA CCC CCC CGG AAG CCT CCT GGG ACT GTC GCT GGC ACA GCC CGA GGC CCT
 S   G   P   P   R   K   P   P   G   T   V   A   G   T   A   R   G   P
      1521            1530            1539            1548            1557            1566
GAA GGT AGC ACG GCT CAG GTG CCA GCA GCA TCA CCG CCG GAG
 E   G   S   T   A   Q   V   P   A   A   S   P   P   E
      1575            1584            1593            1602            1611            1620
GGT CCA GTG CTC ACT TTC CAG AGT GAG AAG ATG AAG GGC ATG AAG GAG CTG CTG
 G   P   V   L   T   F   Q   S   E   K   M   K   G   M   K   E   L   L
      1629            1638            1647            1656            1665            1674
GTG GCC ACC AAG ATC AAC TCG AGC GCC ATC AAG CTG CAA CTC ACG GCA CAG TCG
 V   A   T   K   I   N   S   S   A   I   K   L   Q   L   T   A   Q   S
      1683            1692            1701            1710            1719            1728
CAA GTG CAG ATG AAG AAG CAG AAA GTG TCC ACC CCT AGT GAC TAC ACT CTG TCT
 Q   V   Q   M   K   K   Q   K   V   S   T   P   S   D   Y   T   L   S
      1737            1746            1755            1764            1773            1782
TTC CTC AAG CGG CAG GCA AAA GGC CTC TGA ACT ACT GGG GAC TTC GGA CCG CTT
 F   L   K   R   Q   A   K   G   L
```

FIGURE 1D

```
        1791            1800            1809            1818            1827            1836
GTG GGG ACC CAG GCT CCG CCC TTA GTC CCC CAA CTC TGA GCC CAT GTT CTG CCC
        1845            1854            1863            1872            1881            1890
CCA GCC CAA AGG GGA CAG GCC TCA CCT CTA CCC AAA CCC TAG GTT CCC GGT CCC
        1899            1908            1917            1926            1935            1944
GAG TAC AGT CTG TAT CAA ACC CAC GAT TTT CTC CAG CTC AGA ACC CAG GGC TCT
        1953            1962            1971            1980            1989            1998
GCC CCA GTC GTT AGA ATA TAG GTC TCT TCT CCC AGA ATC CCA GCC GGC MAA TGG
        2007            2016            2025            2034            2043            2052
AAA CCT CAC GCT GGG TCC TAA TTA CCA GTC TTT AAA GGC CCA GCC CCT AGA AAC
        2061            2070            2079            2088            2097            2106
CMA AGC TCN TCC TCG GNA ACC GYT CAC CTA GAG CCA GAC CAA CGT TAY TCA GGG
        2115            2124            2133            2142            2151            2160
GTC CTN CCA GCT TGT AGG AGC TGA GGT TTN ACC CTT NAC CCA AGG AGG AAA NGG
        2169            2178            2187            2196
TCC CAN CTT CAG CCC GGG AGN CTA GGA CAN NCA GGC 3'
```

| SEQ ID | SEQUENCE | LIBRARY | CANCER ASSOCIATION |
|---|---|---|---|
| 26591 | EST | SPLNFET01 | NO |
| 26592 | EST | SPLNFET01 | NO |
| 335704 | EST | EOSIHET02 | NO |
| 391945 | EST | TMLR2DT01 | NO |
| 604021 | EST | BRSTTUT01 | YES; GRADE 4 BREAST CARCINOMA |
| 794402 | EST | OVARNOT03 | YES; GRADE 2 CYSTADENOCARCINOMA |
| 798150 | EST | OVARNOT03 | YES; GRADE 2 CYSTADENOCARCINOMA |
| 955492 | EST | KIDNNOT05 | NO |
| 1214793 | EST | BRSTTUT01 | YES; GRADE 4 BREAST CARCINOMA |
| 1232634 | EST | LUNGFET03 | NO |
| 1290734 | EST | BRAINOT11 | NO |
| 1290749 | EST | BRAINOT11 | NO |
| 1299262 | EST | BRSTNOT07 | YES; GRADE 4 BREAST CARCINOMA |
| 1313372 | EST | BLADTUT02 | YES; TRANSITIONAL CELL CARCINOMA |
| 1355220 | EST | LUNGNOT09 | NO |
| 1381122 | EST | BRAITUT08 | YES; ASTROCYTOMA |
| 1381650 | EST | BRAITUT08 | YES; ASTROCYTOMA |
| 1450878 | LR | PENITUT01 | YES; SQUAMOUS CELL CARCINOMA |
| 1450883 | EST | PENITUT01 | YES; SQUAMOUS CELL CARCINOMA |
| 1577445 | EST, LR | LNODNOT03 | YES; LUNG CANCER |
| 1596949 | EST, LR | BRAINOT14 | YES; ASTROCYTOMA |
| 1597253 | EST | BRAINOT14 | YES; ASTROCYTOMA |
| 1628633 | EST | COLNPOT01 | YES; ADENOCARCINOMA |
| 1655328 | EST | PROSTUT08 | YES; ADENOCARCINOMA |
| 1693847 | EST | COLNNOT23 | NO |
| 1845962 | EST, LR | COLNNOT09 | YES; ADENOCARCINOMA |
| 1872080 | EST | LEUKNOT02 | NO |
| 1968784 | EST | BRSTNOT04 | YES; GRADE 3 BREAST CARCINOMA |
| 2004995 | EST | TESTNOT03 | NO |

FIGURE 3A

| | | | |
|---|---|---|---|
| 2008473 | EST | TESTNOT03 | NO |
| 2097134 | EST | BRAITUT02 | YES; HYPERNEPHROMA |
| 2105784 | EST | BRAITUT03 | YES; ASTROCYTOMA |
| 2111529 | EST | BRAITUT03 | YES; ASTROCYTOMA |
| 2113877 | EST | BRAITUT03 | YES; ASTROCYTOMA |
| 2194826 | EST | THYRTUT03 | NO; BENIGN THYROID TUMOR |
| 2212438 | EST | SINTFET03 | NO |
| 2232432 | EST | PROSNOT16 | YES; ADENOCARCINOMA |
| 2294136 | EST | BRAINON01 | YES; OLIGOASTROCYTOMA |
| 2304470 | EST | BRSTNOT05 | YES; GRADE 4 BREAST CARCINOMA |
| 2395947 | EST | THP1AZT01 | NO |
| 2416332 | EST | HNT3AZT01 | YES; STIMULATED TERATOCARCINOMA CELL LINE |
| 2482430 | EST | SMCANOT01 | NO |
| 2515849 | EST | LIVRTUT04 | YES; HEPATOMA |
| 2675883 | EST | KIDNNOT19 | YES; RENAL CELL CARCINOMA |
| 2809030 | EST | BLADTUT08 | YES; TRANSITIONAL CELL CARCINOMA |
| 2809229 | EST | BLADTUT08 | YES; TRANSITIONAL CELL CARCINOMA |
| 2811751 | EST | OVARNOT10 | NO |
| 2811824 | EST | OVARNOT10 | NO |
| 2954873 | EST | KIDNFET01 | NO |
| 3143320 | EST | HNT2AZS07 | YES; STIMULATED TERATOCARCINOMA CELL LINE |
| 3143537 | EST | HNT2AZS07 | YES; STIMULATED TERATOCARCINOMA CELL LINE |
| G1087216 | DBEST | LIVSFEM02 | NO |
| G1087217 | DBEST | LIVSFEM02 | NO |
| G1118253 | DBEST | MELANOM01 | NO |
| G1138306 | DBEST | MELANOM01 | NO |
| G1157332 | DBEST | MELANOM01 | NO |
| G1166905 | DBEST | MELANOM01 | NO |
| G1192940 | DBEST | NERVMSM01 | NO |
| G1320152 | DBEST | LUNGFEM01 | NO |

FIGURE 3B

| | | | |
|---|---|---|---|
| G1443404 | DBEST | LUNGFEM01 | NO |
| G1716991 | DBEST | UTRPNOM01 | NO |
| G1717047 | DBEST | UTRPNOM01 | NO |
| G1729182 | DBEST | PANCTUM01 | YES; ADENOCARCINOMA |
| G1732684 | DBEST | PANCTUM01 | YES; ADENOCARCINOMA |
| G1732684 | DBEST | PANCTUM01 | YES; ADENOCARCINOMA |
| G1807419 | DBEST | HNTNNOM01 | YES; STIMULATED TERATOCARCINOMA CELL LINE |
| G1810031 | DBEST | HNTNNOM01 | YES; STIMULATED TERATOCARCINOMA CELL LINE |
| G784623 | DBEST | PLACNOM02 | NO |
| G788522 | DBEST | PLACNOM02 | NO |
| G879097 | DBEST | BRAINOM02 | NO |
| G879101 | DBEST | BRAINOM02 | NO |
| G879120 | DBEST | BRAINOM02 | NO |
| G879133 | DBEST | BRAINOM02 | NO |
| G881170 | DBEST | BRAINOM01 | NO |
| G907795 | DBEST | BRAINOM02 | NO |
| G907832 | DBEST | BRAINOM02 | NO |
| G917403 | DBEST | BRAINOM02 | NO |
| G985126 | DBEST | LIVSFEM02 | NO |

FIGURE 3C

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 564 amino acids
       (B) TYPE: amino acid
       (C) STRANDEDNESS: single
       (D) TOPOLOGY: linear (vii) IMMEDIATE SOURCE:
       (A) LIBRARY: BRAINOT14
       (B) CLONE: Consensus (xi) SEQUENCE DESCRIPTION: SEQ ID NO:1:

```
Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
            35                  40                  45

Ala Val Asn Arg Val Ile Pro Thr Asn Val Pro Glu Leu Thr Phe Gln
50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
            85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
            115                 120                 125

Leu Ser Arg Ser Tyr Phe Lys Asp Xaa Ala His Ile Gln Ser Leu Phe
            130                 135                 140

Ser Phe Ile Thr Gly Thr Lys Leu Asp Ser Gly Val Ala Phe Ala Val
145                 150                 155                 160

Gly Pro Asn Gly Glu Gln Thr Ala Glu Val Thr Trp His Gly Lys Gly
                165                 170                 175

Asn Glu Asp Arg Arg Gly Gln Thr Val Asn Ala Gly Val Ala Glu Arg
            180                 185                 190

Ser Trp Leu Tyr Leu Lys Gly Ser Tyr Met Arg Cys Asp Arg Lys Met
            195                 200                 205

Glu Val Ala Phe Met Val Cys Ala Ile Asn Pro Ser Ile Asp Leu His
210                 215                 220

Thr Asp Ser Leu Glu Leu Leu Gln Leu Gln Gln Lys Leu Leu Trp Leu
225                 230                 235                 240

Leu Tyr Asp Leu Gly His Leu Glu Arg Tyr Pro Met Ala Leu Gly Asn
                245                 250                 255

Leu Ala Asp Leu Glu Glu Leu Glu Pro Thr Pro Gly Arg Pro Asp Pro
            260                 265                 270

Xaa Ala Leu Leu His Lys Gly Ile Ala Ser Ala Lys Thr Tyr Tyr Arg
            275                 280                 285

Asp Glu His Ile Tyr Pro Tyr Met Tyr Leu Ala Gly Tyr His Cys Arg
            290                 295                 300

Asn Arg Asn Val Arg Glu Xaa Leu Gln Ala Leu Gly Arg Asp Thr Ala
```

```
                305                 310                 315                 320
Thr Leu Ile Gln Asp Tyr Asn Tyr Cys Arg Glu Asp Glu Ile Tyr
                    325                 330                 335
Lys Glu Phe Phe Glu Val Ala Asn Asp Val Ile Pro Asn Leu Leu Lys
            340                 345                 350
Glu Ala Ala Ser Leu Leu Glu Ala Gly Glu Glu Arg Pro Gly Glu Gln
            355                 360                 365
Ser Gln Gly Thr Gln Ser Gln Gly Ser Ala Leu Gln Asp Pro Glu Cys
        370                 375                 380
Phe Ala His Leu Leu Arg Phe Tyr Asp Gly Ile Cys Lys Trp Glu Glu
385                 390                 395                 400
Gly Ser Pro Thr Pro Val Leu His Val Gly Trp Ala Pro Phe Leu Xaa
                405                 410                 415
Gln Ser Leu Xaa Arg Phe Xaa Gly Gln Val Xaa Gln Lys Val Arg Ile
            420                 425                 430
Val Xaa Arg Asp Ala Glu Ala Ala Glu Lys Pro Glu Glu Pro Pro Pro
            435                 440                 445
Pro Lys Lys Pro Ala Leu Asp Lys Gly Leu Gly Thr Gly Gln Gly Ala
    450                 455                 460
Val Ser Gly Pro Pro Arg Lys Pro Pro Gly Thr Val Ala Gly Thr Ala
465                 470                 475                 480
Arg Gly Pro Glu Gly Gly Ser Thr Ala Gln Val Pro Ala Pro Ala Ala
                485                 490                 495
Ser Pro Pro Pro Glu Gly Pro Val Leu Thr Phe Gln Ser Glu Lys Met
            500                 505                 510
Lys Gly Met Lys Glu Leu Leu Val Ala Thr Lys Ile Asn Ser Ser Ala
        515                 520                 525
Ile Lys Leu Gln Leu Thr Ala Gln Ser Gln Val Gln Met Lys Lys Gln
        530                 535                 540
Lys Val Ser Thr Pro Ser Asp Tyr Thr Leu Ser Phe Leu Lys Arg Gln
545                 550                 555                 560
Ala Lys Gly Leu (2) INFORMATION FOR SEQ ID NO:2:

(i) SEQUENCE CHARACTERISTICS:
        (A) LENGTH: 2196 base pairs
        (B) TYPE: nucleic acid
        (C) STRANDEDNESS: single
        (D) TOPOLOGY: linear (vii) IMMEDIATE SOURCE:
        (A) LIBRARY: BRAINOT14
        (B) CLONE: Consensus (xi) SEQUENCE DESCRIPTION: SEQ ID NO:2:

NANGCGGCGT GCGCCGCGGT GCCTAGTGTG GGATGCCGCC GCCCACCGCC CGCCGCCATG       60

GGGCTGAAGG CCGCCCAGAA GACGCTGTTC CCGCTGCGCT CCATCGACGA CGTGGTGCGC      120

CTGTTTGCTG CCGAGCTGGG CCGAGAGGAG CCGGACCTGG TGCTCCTTTC CTTGGTGCTG      180

GGCTTCGTGG AGCATTTTCT GGCTGTCAAC CGCGTCATCC CTACCAACGT TCCCGAGCTC      240

ACCTTCCAGC CCAGCCCCGC CCCCGACCCG CCTGGCGGCC TCACCTACTT TCCCGTGGCC      300

GACCTGTCTA TCATCGCCGC CCTCTATGCC CGCTTCACCG CCCAGATCCG AGGCGCCGTC      360

GACCTGTCCC TCTATCCTCG AGAAGGGGGT GTCTCCAGCC GTGAGCTGGT GAAGAAGGTC      420

TCCGATGTCA TATGGAACAG CCTCAGCCGC TCCTACTTCA AGGATYGGGC CCACATCCAG      480
```

```
TCCCTCTTCA GCTTCATCAC AGGCACCAAA TTGGACTCCG GNGTGGCCTT TGCTGTGNNT      540

GGGCCCAATG GGGAGCAGAC AGCTGAGGTC ACCTGGCACG GCAAGGGCAA CGAGGACCGC      600

AGGGGCCAGA CAGTCAATGC CGGTGTGGCT GAGCGGAGCT GGCTGTACCT GAAAGGATCA      660

TACATGCGCT GTGACCGCAA GATGGAGGTG GCGTTCATGG TGTGTGCCAT CAACCCTTCC      720

ATTGACCTGC ACACCGACTC GCTGGAGCTT CTGCAGCTGC AGCAGAAGCT GCTCTGGCTG      780

CTCTATGACC TGGGACATCT GGAAAGGTAC CCCATGGCCT TAGGGAACCT GGCAGATCTA      840

GAGGAGCTGG AGCCCACCCC TGGCCGGCCA GACCCSRGGG CGCTGCTRCA CAAGGGCATT      900

GCTTCAGCCA AGACCTACTA TCGGGATGAA CACATCTACC CCTACATGTA CCTGGCTGGC      960

TACCACTGTC GCAACCGCAA TGTGCGGGAA SCCCTGCAGG CCCTRGGCAG AGACACGGCC     1020

ACTCTCATCC AGGACTACAA CTACTGCCGG GAAGACGAGG AGATCTACAA GGAGTTCTTT     1080

GAAGTAGCCA ATGATGTCAT CCCCAACCTG CTGAAGGAGG CAGCCAGCTT GCTGGAGGCG     1140

GGCGAGGAGC GGCCGGGGGA GCAAAGCCAG GGCACCCAGA GCCAAGGTTC CGCCCTCCAG     1200

GACCCTGAGT GCTTCGCCCA CCTGCTGCGA TTCTACGACG GCATCTGCAA ATGGGAGGAG     1260

GGCAGTCCCA CGCCTGTGCT GCACGTGGGC TGGGCACCTT TCTTGTNGCA GTCCCTANGC     1320

CGTTTTGANG GACAGGTGCN GCAGAAGGTG CGCATAGTGA NCCGAGATGC CGAGGCTGCC     1380

GAGNCCAAGC CAGAGGAGCC CCCGCCGCCC AAGAAGCCAG CACTGGACAA GGGCCTGGGC     1440

ACCGGCCAGG GCGCAGTGTC AGGACCCCCC CGGAAGCCTC CTGGGACTGT CGCTGGCACA     1500

GCCCGAGGCC CTGAAGGTGG CAGCACGGCT CAGGTGCCAG CACCCGCAGC ATCACCACCG     1560

CCGGAGGGTC CAGTGCTCAC TTTCCAGAGT GAGAAGATGA AGGGCATGAA GGAGCTGCTG     1620

GTGGCCACCA AGATCAACTC GAGCGCCATC AAGCTGCAAC TCACGGCACA GTCGCAAGTG     1680

CAGATGAAGA AGCAGAAAGT GTCCACCCCT AGTGACTACA CTCTGTCTTT CCTCAAGCGG     1740

CAGGCAAAAG GCCTCTGAAC TACTGGGGAC TTCGGACCGC TTGTGGGGAC CCAGGCTCCG     1800

CCCTTAGTCC CCCAACTCTG AGCCCATGTT CTGCCCCCAG CCCAAAGGGG ACAGGCCTCA     1860

CCTCTACCCA AACCCTAGGT TCCCGGTCCC GAGTACAGTC TGTATCAAAC CCACGATTTT     1920

CTCCAGCTCA GAACCCAGGG CTCTGCCCCA GTCGTTAGAA TATAGGTCTC TTCTCCCAGA     1980

ATCCCAGCCG GCMAATGGAA ACCTCACGCT GGGTCCTAAT TACCAGTCTT TAAAGGCCCA     2040

GCCCCTAGAA ACCMAAGCTC NTCCTCGGNA ACCGYTCACC TAGAGCCAGA CCAACGTTAY     2100

TCAGGGGTCC TNCCAGCTTG TAGGAGCTGA GGTTTNACCC TTNACCCAAG GAGGAAANGG     2160

TCCCANCTTC AGCCCGGGAG NCTAGGACAN NCAGGC                              2196

(2) INFORMATION FOR SEQ ID NO:3:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (vii) IMMEDIATE SOURCE:
        (A) LIBRARY: BRAINOT14
        (B) CLONE: 1596949

(xi) SEQUENCE DESCRIPTION: SEQ ID NO:3:

ANGCGGCGTG CGCCGCGGTG CCTAGTGTGG GATGCCGCCG CCCACCGCCC GCCGCCATGG       60

GGCTGAAGGC CGCCCAGAAG ACGCTGTTCC CGCTGCGCTC CATCGACGAC GTGGTGCGCC      120

TGTTTGCTGC CGAGCTGGGC CGAGAGGAGC CGGACCTGGT GCTCCTTTCC TTGGTGCTGG      180

GCTTCGTGGA GCATTTTCTG GCTGTCAACC GCGTCATCCC TACCAACGTT CCCGAGCTCA      240
```

```
CCTTCCAGCC CAGCCCCGCC CCCGACCCGC CTGGCGGCCT CACCTACTTT CCCGTGGCCG      300

ACCTGTCTAT CATCGCCGCC CTCTATGCCC GCTTCACCGC CCAGATCCGA GGCGCCGTCG      360

ACCTGTCCCT CTATCCTCGA AAGGGGGTG TCTCCAGCCG TGAGCTGGTG AAGAAGGTCT       420

CCGATGTCAT ATGGAACAGC CTCAGCCGCT CCTACTTCAA GGATYGGGCC CACATCCAGT     480

CCCTCTTCAG CTTCATCACA GGCACCAAAT TGGACASTCC GGNGTGGCCT TTGCTGTG       538
```

(2) INFORMATION FOR SEQ ID NO:4:

(i) SEQUENCE CHARACTERISTICS:
        (A) LENGTH: 986 base pairs
        (B) TYPE: nucleic acid
        (C) STRANDEDNESS: single
        (D) TOPOLOGY: linear (vii) IMMEDIATE SOURCE:
        (A) LIBRARY: BLADTUT08
        (B) CLONE: 2809030

(xi) SEQUENCE DESCRIPTION: SEQ ID NO:4:

```
TGGGCCCAAT GGGGAGCAGA CAGCTGAGGT CACCTGGCAC GGCAAGGGCA ACGAGGACCG      60

CAGGGGCCAG ACAGTCAATG CCGGTGTGGC TGAGCGGAGC TGGCTGTACC TGAAAGGATC     120

ATACATGCGC TGTGACCGCA AGATGGAGGT GGCGTTCATG GTGTGTGCCA TCAACCCTTC     180

CATTGACCTG CACACCGACT CGCTGGAGCT TCTGCAGCTG CAGCAGAAGC TGCTCTGGCT     240

GCTCTATGAC CTGGGACATC TGGAAAGGTA CCCCATGGCC TTAGGGAACC TGGCAGATCT     300

AGAGGAGCTG GAGCCCACCC CTGGCCGGCC AGACCCSRGG GCGCTGCTRC ACAAGGGCAT     360

TGCTTCAGCC AAGACCTACT ATCGGGATGA ACACATCTAC CCCTACATGT ACCTGGCTGG     420

CTACCACTGT CGCAACCGCA ATGTGCGGGA ASCCCTGCAG GCCCTRGGCA GAGACACGGC     480

CACTCTCATC CAGGACTACA ACTACTGCCG GGAAGACGAG GAGATCTACA AGGAGTTCTT     540

TGAAGTAGCC AATGATGTCA TCCCCAACCT GCTGAAGGAG GCAGCCAGCT TGCTGGAGGC     600

GGGCGAGGAG CGGCCGGGGG AGCAAAGCCA GGGCACCCAG AGCCAAGGTT CCGCCCTCCA     660

GGACCCTGAG TGCTTCGCCC ACCTGCTGCG ATTCTACGAC GGCATCTGCA AATGGGAGGA     720

GGGCAGTCCC ACGCCTGTGC TGCACGTGGG CTGGGCACCT TTCTTGTNGC AGTCCCTANG     780

CCGTTTTGAN GGACAGGTGC NGCAGAAGGT GCGCATAGTG ANCCGAGATG CCGAGGCTGC     840

CGAGGCCANG AGCCGTGGNG CTAGGAAGCC CGGNAANGCC GGCNGNNGGG CCCACNGCAG     900

GAGTCCAAGC CANATGAGCN NCCNCCGCNC AANNAGCNAN NANGGACNAG GNCCTTGGGC     960

NCCGGCCAGN GTGNATNTCA TGNCNC                                         986
```

(2) INFORMATION FOR SEQ ID NO:5:

(i) SEQUENCE CHARACTERISTICS:
        (A) LENGTH: 812 base pairs
        (B) TYPE: nucleic acid
        (C) STRANDEDNESS: single
        (D) TOPOLOGY: linear (vii) IMMEDIATE SOURCE:
        (A) LIBRARY: BLADTUT02
        (B) CLONE: 1313372

(xi) SEQUENCE DESCRIPTION: SEQ ID NO:5:

```
CCAAGCCAGA GGAGCCCCCG CCGCCCAAGA AGCCAGCACT GGACAAGGGC CTGGGCACCG      60

GCCAGGGCGC AGTGTCAGGA CCCCCCCGGA AGCCTCCTGG GACTGTCGCT GGCACAGCCC     120

GAGGCCCTGA AGGTGGCAGC ACGGCTCAGG TGCCAGCACC CGCAGCATCA CCACCGCCGG    180
```

-continued

```
AGGGTCCAGT GCTCACTTTC CAGAGTGAGA AGATGAAGGG CATGAAGGAG CTGCTGGTGG    240

CCACCAAGAT CAACTCGAGC GCCATCAAGC TGCAACTCAC GGCACAGTCG CAAGTGCAGA    300

TGAAGAAGCA GAAAGTGTCC ACCCCTAGTG ACTACACTCT GTCTTTCCTC AAGCGGCAGG    360

CAAAAGGCCT CTGAACTACT GGGGACTTCG GACCGCTTGT GGGGACCCAG GCTCCGCCCT    420

TAGTCCCCCA ACTCTGAGCC CATGTTCTGC CCCCAGCCCA AAGGGGACAG GCCTCACCTC    480

TACCCAAACC CTAGGTTCCC GGTCCCGAGT ACAGTCTGTA TCAAACCCAC GATTTTCTCC    540

AGCTCAGAAC CCAGGGCTCT GCCCCAGTCG TTAGAATATA GGTCTCTTCT CCCAGAATCC    600

CAGCCGGCMA ATGGAAACCT CACGCTGGGT CCTAATTACC AGTCTTTAAA GGCCCAGCCC    660

CTAGAAACCM AAGCTCNTCC TCGGNAACCG YTCACCTAGA GCCAGACCAA CGTTAYTCAG    720

GGGTCCTNCC AGCTTGTAGG AGCTGAGGTT TNACCCTTNA CCCAAGGAGG AAANGGTCCC    780

ANCTTCAGCC CGGGAGNCTA GGACANNCAG GC                                  812
```

(2) INFORMATION FOR SEQ ID NO:6:

(i) SEQUENCE CHARACTERISTICS:
        (A) LENGTH: 610 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1945387

(xi) SEQUENCE DESCRIPTION: SEQ ID NO:6:

```
Met Gly Leu Lys Ala Ala Gln Lys Thr Leu Phe Pro Leu Arg Ser Ile
 1               5                  10                  15

Asp Asp Val Val Arg Leu Phe Ala Ala Glu Leu Gly Arg Glu Glu Pro
                20                  25                  30

Asp Leu Val Leu Leu Ser Leu Val Leu Gly Phe Val Glu His Phe Leu
            35                  40                  45

Ala Val Asn Arg Val Ile Pro Thr Asn Val Pro Glu Leu Thr Phe Gln
        50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
                100                 105                 110

Ser Ser Arg Glu Leu Val Lys Lys Val Ser Asp Val Ile Trp Asn Ser
            115                 120                 125

Leu Ser Arg Ser Tyr Phe Lys Asp Arg Ala His Ile Gln Ser Leu Phe
        130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Val Val Phe Gly Pro Asn Gly Glu Gln
                180                 185                 190

Thr Ala Glu Val Thr Trp His Gly Lys Gly Asn Glu Asp Arg Arg Gly
            195                 200                 205

Gln Thr Val Asn Ala Gly Val Ala Glu Arg Ser Trp Leu Tyr Leu Lys
        210                 215                 220
```

```
Gly Ser Tyr Met Arg Cys Asp Arg Lys Met Glu Val Ala Phe Met Val
225                 230                 235                 240

Cys Ala Ile Asn Pro Ser Ile Asp Leu His Thr Asp Ser Leu Glu Leu
            245                 250                 255

Leu Gln Leu Gln Gln Lys Leu Leu Trp Leu Leu Tyr Asp Leu Gly His
        260                 265                 270

Leu Glu Arg Tyr Pro Met Ala Leu Gly Asn Leu Ala Asp Leu Glu Glu
    275                 280                 285

Leu Glu Pro Thr Pro Gly Arg Pro Asp Pro Leu Thr Leu Tyr His Lys
290                 295                 300

Gly Ile Ala Ser Ala Lys Thr Tyr Tyr Arg Asp His Ile Tyr Pro
305                 310                 315                 320

Tyr Met Tyr Leu Ala Gly Tyr His Cys Arg Asn Arg Asn Val Arg Glu
            325                 330                 335

Ala Leu Gln Ala Trp Ala Asp Thr Ala Thr Val Ile Gln Asp Tyr Asn
        340                 345                 350

Tyr Cys Arg Glu Asp Glu Glu Ile Tyr Lys Glu Phe Phe Glu Val Ala
    355                 360                 365

Asn Asp Val Ile Pro Asn Leu Leu Lys Glu Ala Ala Ser Leu Leu Glu
370                 375                 380

Ala Gly Glu Glu Arg Pro Gly Glu Gln Ser Gln Gly Thr Gln Ser Gln
385                 390                 395                 400

Gly Ser Ala Leu Gln Asp Pro Glu Cys Phe Ala His Leu Leu Arg Phe
            405                 410                 415

Tyr Asp Gly Ile Cys Lys Trp Glu Glu Gly Ser Pro Thr Pro Val Leu
        420                 425                 430

His Val Gly Trp Ala Thr Phe Leu Val Gln Ser Leu Gly Arg Phe Glu
    435                 440                 445

Gly Gln Val Arg Gln Lys Val Arg Ile Val Ser Arg Glu Ala Glu Ala
450                 455                 460

Ala Glu Ala Glu Glu Pro Trp Gly Glu Glu Ala Arg Glu Gly Arg Arg
465                 470                 475                 480

Arg Gly Pro Arg Arg Glu Ser Lys Pro Glu Glu Pro Pro Pro Pro Lys
            485                 490                 495

Lys Pro Ala Leu Asp Lys Gly Leu Gly Thr Gly Gln Gly Ala Val Ser
        500                 505                 510

Gly Pro Pro Arg Lys Pro Pro Gly Thr Val Ala Gly Thr Ala Arg Gly
    515                 520                 525

Pro Glu Gly Gly Ser Thr Ala Gln Val Pro Ala Pro Ala Ala Ser Pro
530                 535                 540

Pro Pro Glu Gly Pro Val Leu Thr Phe Gln Ser Glu Lys Met Lys Gly
545                 550                 555                 560

Met Lys Glu Leu Leu Val Ala Thr Lys Ile Asn Ser Ser Ala Ile Lys
```

-continued

```
                  565                 570                575

Leu Gln Leu Thr Ala Gln Ser Gln Val Gln Met Lys Lys Gln Lys Val
                580                 585                590

Ser Thr Pro Ser Asp Tyr Thr Leu Ser Phe Leu Lys Arg Gln Arg Lys
            595                 600                605

Gly Leu
    610
```

POLYNUCLEOTIDE SEQUENCE ENCODING HUMAN MULTIPLE ENDOCRINE NEOPLASIA TYPE 1 PROTEIN

FIELD OF THE INVENTION

This invention relates to nucleic acid and amino acid sequences of a human multiple endocrine neoplasia type 1 protein and to the use of these sequences in the diagnosis, prevention, and treatment of multiple endocrine neoplasias.

BACKGROUND OF THE INVENTION

Wermer's syndrome or multiple endocrine neoplasia type 1 (MEN1) is characterized by the neoplastic transformation of parathyroid, pituitary, adrenal, gastric endocrine, and pancreatic islet cells. The gene associated with MEN1, which is inherited as an autosomal dominant, is believed to be a tumor suppressor. Normally tumor suppressors play an important role in the regulation of cell growth; however, in heterozygous individuals, when the normal copy of the gene is mutated through an error in DNA replication, tumor development results.

The MEN1 locus (OMIM * 131100) has been mapped to a minimal interval on chromosome 11q13 bounded centromerically by PYGM (Emmert-Buck M. R. et al. (1996) Science 274:998) and telomerically by D11S4936. The genomic sequence as reconstructed from inserts in YAC, BAC, PAC, and P1 clones consists of 10 exons which encode a 2.8 kb transcript. The sequence mu was assembled from 44 different ESTs in NCBI dbEST and from shotgun sequence assemblies. Northern blots using a 1.9 kb contig of the human sequences showed expression in all tissues tested (pancreas, adrenal medulla, thyroid, small intestine, stomach, spleen, prostate, ovary, in colon and in leukocytes. Five frameshift mutations, three nonsense mutations, two deletions, and two missense alterations in this sequence have been identified (Chandrasekharappa, S. C. et al. (1997) Science 276:404–407).

MEN1 syndrome is known to evolve and worsen over a 30 to 40-year period during which cellular mutations increase and the efficiency of the cellular machinery and its their ability to repair chromosomal lesions decreases. The syndrome begins with transformation of a single cell to hyperplasia and progresses through adenomatous or carcinomatous changes. It is known that the neoplastic process, especially hormone production in one gland or organ, may affect progression and manifestation of MEN1 and associated syndromes in another gland or organ.

Neoplasia of the pancreatic islets is common to 80% of MEN1 patients and tends to occur in parallel with parathyroid problems. The excess hormones commonly produced by pancreatic islet cell are pancreatic polypeptide, gastrin, insulin, vasoactive intestinal peptide, glucagon, and somatostatin. Other peptides such as adrenocorticotropin (ACTH), corticotropin-releasing hormone (CRH), growth hormone-releasing hormone (GHRH), calcitonin gene products, neurotensin, and gastric inhibitory peptide, may be produced by MEN1 tumors depending on the stage of the disease. Since some MEN1 neoplasms develop malignant features and metastasize to other organs, aggressive screening and surgical intervention at an early stage are very important.

Syndromes associated with neoplasia of the pancreatic islets include Zollinger-Ellison syndrome, Verner-Morrison syndrome, insulinoma, and glucagonoma. Zollinger-Ellison syndrome is characterized by increased gastric acid production, recurrent peptic ulcers, diarrhea, and esophagitis. Verner-Morrison syndrome appears to be associated with the overproduction of vasoactive intestinal peptide and manifests as watery diarrhea, hypokalemia, hypochlorhydria, hypercalcemia, and systemic acidosis. Insulinomas overproduce insulin and cause symptoms such as nervousness, sweating, palpitations, excessive hunger or weight gain, seizures, and loss of consciousness in the fasting state. Glucagonoma is characterized by symptoms such as hyperglycemia, skin rash, anorexia, glossitis, anemia, depression, diarrhea, and venous thrombosis.

Multicentric pituitary tumors occur in over 50% of mutant MEN1 gene carriers. These tumors may cause galactorrhea-amenorrhea syndrome, acromegaly due to excessive growth hormone or GHRH production, or Cushing's disease attributable to excess amounts of ACTH or CRH. MEN1 also manifests as metastasizing carcinoid tumors of the gastrointestinal system. These tumors commonly result from lesions in stomach or duodenal endocrine cells or originate in the thymus or lung. The carcinoid tumors may or may not be locally invasive, and commonly produce serotonin, calcitonin, or CRH.

The discovery of a new human multiple endocrine neoplasia type 1 protein and the polynucleotides encoding it satisfies a need in the art by providing new compositions which are useful in the diagnosis, prevention, and treatment of multiple endocrine neoplasia.

SUMMARY OF THE INVENTION

The invention features a substantially purified polypeptide, human multiple endocrine neoplasia type 1 protein (MEND1), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof. In another aspect the invention provides a composition comprising an isolated and purified polynucleotide sequence encoding MEND1. In a particular aspect, the polynucleotide is the nucleotide sequence of SEQ ID NO:2 or variants thereof.

In addition, the invention provides a polynucleotide sequence which hybridizes under stringent conditions to the polynucleotide sequence of SEQ ID NO:2.

The invention further provides a polynucleotide sequence comprising the complement of the polynucleotide sequence encoding the amino acid sequence of SEQ ID NO:1, or fragments or variants thereof. In a particular aspect, the polynucleotide sequence is the complement of SEQ ID NO:2. In another aspect, the invention provides a composition comprising an isolated and purified polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding MEND1 under conditions suitable for the expression of the polypeptide; and b) recovering the polypeptide from the host cell culture.

The invention also provides a pharmaceutical composition comprising a substantially purified MEND1 having the amino acid sequence of SEQ ID NO:1 in conjunction with a suitable pharmaceutical carrier.

The invention also provides a method for treating or preventing multiple endocrine neoplasia comprising administering to the cells of a subject in need of such treatment an effective amount of a pharmaceutical composition comprising purified MEND1.

The invention also provides a method for treating or preventing multiple endocrine neoplasia comprising administering to the cells of a subject in need of such treatment an expression vector containing the polynucleotide sequence encoding MEND1.

The invention also provides a method for treating or preventing multiple endocrine neoplasia comprising administering to the cells of a subject in need of such treatment a human artificial chromosome containing the polynucleotide sequence encoding MEND1.

The invention also provides a method for detecting a polynucleotide which encodes MEND1 in a biological sample comprising the steps of: a) hybridizing a polynucleotide sequence complementary to MEND1 (SEQ ID NO:1) to nucleic acid material of a biological sample, thereby forming a hybridization complex; and b) detecting the hybridization complex, wherein the presence of the complex correlates with the presence of a polynucleotide encoding MEND1 in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C, 1D and 1E show the amino acid sequence (SEQ ID NO:1) and nucleic acid sequence (SEQ ID NO:2) of MEND1. The alignment was produced using MACDNASIS PRO software (Hitachi Software Engineering Co. Ltd. San Bruno, Calif.).

FIGS. 2A–2B show the amino acid sequence alignments between MEND1 (SEQ ID NO:1) and MEN1 (GI 1945387; SEQ ID NO:6) produced using the multisequence alignment program of DNASTAR software (DNASTAR Inc, Madison Wis.).

FIGS. 3A, 3B and 3C shows the northern analysis for MEND1 which was produced electronically using LIFESEQ database (Incyte Pharmaceuticals, Inc. Palo Alto Calif.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

MEND1, as used herein, refers to the amino acid sequences of substantially purified MEND1 obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to MEND1, increases or prolongs the duration of the effect of MEND1. Agonists may include proteins, nucleic acids, carbohydrates, or any other molecules which bind to and modulate the effect of MEND1.

An "allele" or "allelic sequence", as used herein, is an alternative form of the gene encoding MEND1. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding MEND1 as used herein include those with deletions, insertions, or substitutions of different nucleotides resulting in a polynucleotide that encodes the same or a functionally equivalent MEND1. Included within this definition are polymorphisms which may or may not be readily detectable using a particular oligonucleotide probe of the polynucleotide encoding MEND1, and improper or unexpected hybridization to alleles, with a locus other than the normal chromosomal locus for the polynucleotide sequence encoding MEND1. The encoded protein may also be "altered" and contain deletions, insertions, or substitutions of amino acid residues which produce a silent change and result in a functionally equivalent MEND1. Deliberate amino acid substitutions may be made on the basis of similarity in polarity, charge, solubility, hydrophobicity, hydrophilicity, and/or the amphipathic nature of the residues as long as the biological or immunological activity of MEND1 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of MEND1 are preferably about 5 to about 15 amino acids in length and retain the biological activity or the immunological activity of MEND1. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "antagonist" as used herein, refers to a molecule which, when bound to MEND1, decreases the amount or the duration of the effect of the biological or immunological activity of MEND1. Antagonists may include proteins, nucleic acids, carbohydrates, or any other molecules which decrease the effect of MEND1.

As used herein, the term "antibody" refers to intact molecules as well as fragments thereof, such as Fab, F(ab')$_2$, and Fv, which are capable of binding the epitopic determinant. Antibodies that bind MEND1 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic MEND1, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding MEND1 (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding MEND1 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to MEND1 or the encoded MEND1. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to a high-density array of distinct polynucleotides or oligonucleotides synthesized on a substrate, such as paper, nylon or other type of membrane, filter, chip, glass slide, or any other suitable solid support.

The term "modulate", as used herein, refers to a change in the activity of MEND1. For example, modulation may cause an increase or a decrease in protein activity, binding characteristics, or any other biological, functional or immunological properties of MEND1.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length MEND1 and fragments thereof.

The term "sample", as used herein, is used in its broadest sense. A biological sample suspected of containing nucleic acid encoding MEND1, or fragments thereof, or MEND1 itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of MEND1, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human multiple endocrine neoplasia type 1 protein (hereinafter referred to as MEND1), the polynucleotides encoding MEND1, and the use of these compositions for the diagnosis, prevention, or treatment of multiple endocrine neoplasia.

Nucleic acids encoding the MEND1 of the present invention were first identified in Incyte Clone 1596949 from a brain cDNA library (BRAINOT14) using a computer search for amino acid sequence alignments. A consensus sequence, SEQ ID NO:2, was derived from three overlapping assemblages: Incyte Clones 1596949 (SEQ ID NO:3; BRAINOT14), 2809030 (SEQ ID NO:4; BLADTUT08), and 1313372 (SEQ ID NO:5; BLADTUT02). The following Incyte clones have sequence homologous with MEND1: 26591 and 26592 (SPLNFET01), 335704 (EOSIHET02), 391945 (TMLR2DT01), 604021(BRSTTUT01), 794402 and 798150 (OVARNOT03), 955492 (KIDNNOT05), 1214793 (BRSTTUT01), 1232634 (LUNGFET03), 1290734 and 1290749 (BRAINOT11), 1299262 (BRSTNOT07), 1313372 (BLADTUT02), 1355220 (LUNGNOT09), 1381122 and 1381650 (BRAITUT08), 1450883 (PENITUT01), 1577445 (LNODNOT03), 1596949 and 1597253 (BRAINOT14), 1628633 (COLNPOT01), 1655328 (PROSTUT08), 1693847 (COLNNOT23), 1845962 (COLNNOT09), 1872080 (LEUKNOT02), 1968784 (BRSTNOT04), 2004995 and 2008473 (TESTNOT03), 2097134, 2105784, 2111529, and 2113877 (BRAITUT03), 2194826 (THYRTUT03), 2212438 (SINTFET03), 2232432 (PROSNOT16), 2294136 (BRAINON01), 2304470 (BRSTNOT05), 2395947 (THP1AZT01), 2416332 (HNT3AZT01), 2482430 (SMCANOT01), 2515849 (LIVRTUT04), 2675883 (KIDNNOT19), 2809229 and 2809030 (BLADTUT08), 2811751 and 2811824 (OVARNOT10), 2954873 (KIDNFET01), 3143320 and 3143537 (HNT2AZS07), and 1450878 (PENITUT01).

Figure 2A:
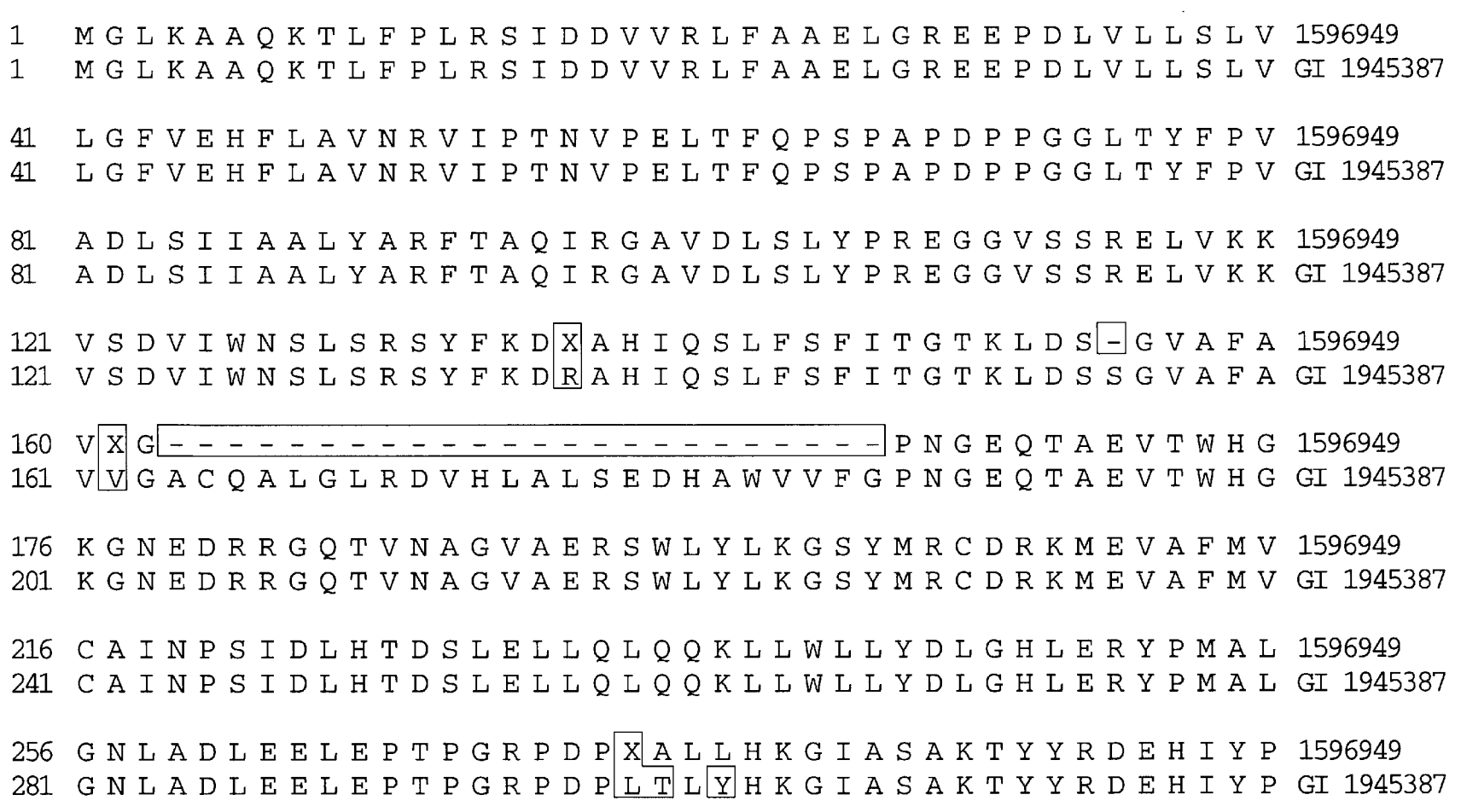
Figure 2B:
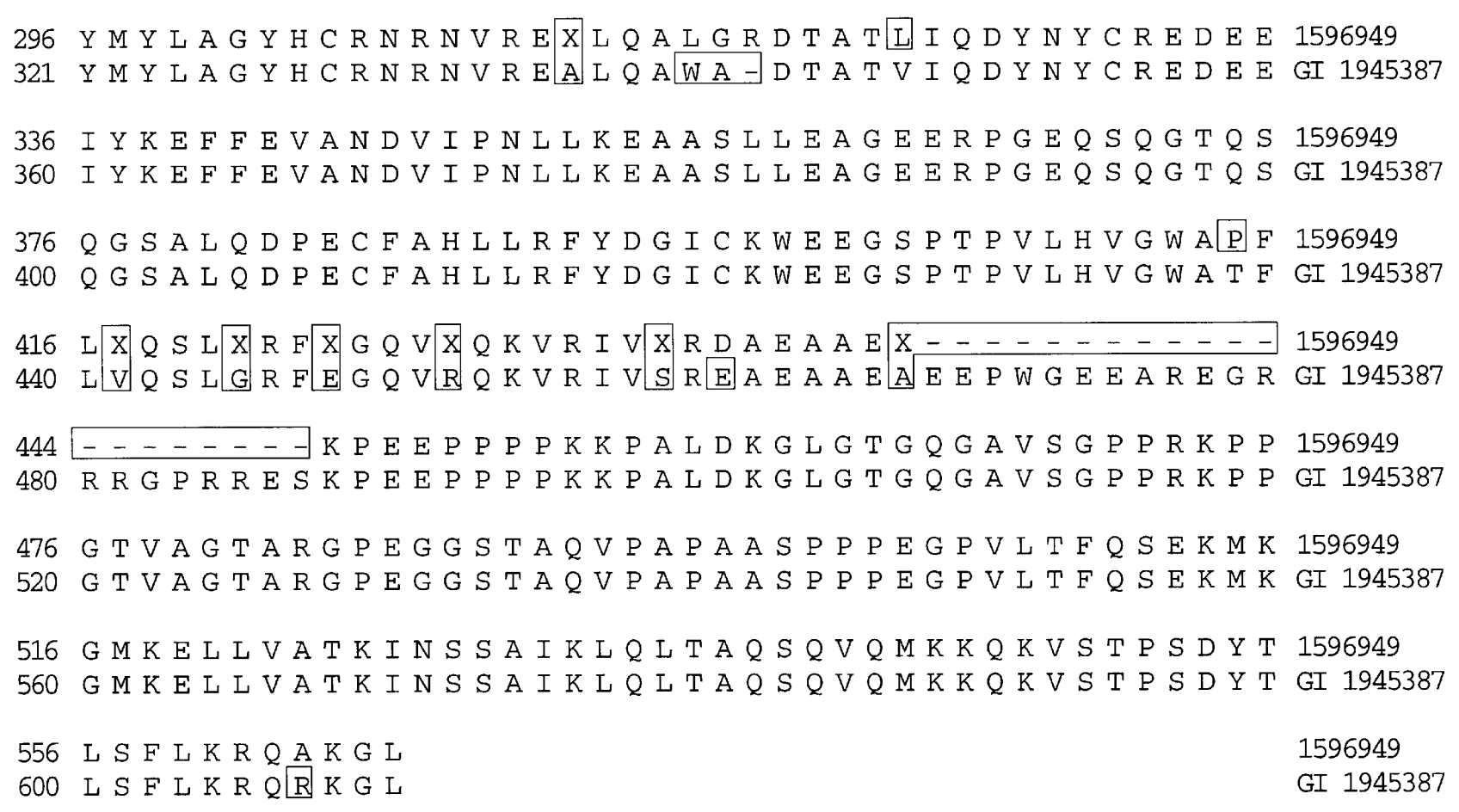

In one embodiment, the invention encompasses a polypeptide comprising the amino acid sequence of SEQ ID NO:1, as shown in FIGS. 1A, 1B, 1C, 1D and 1E. MEND1 is 564 amino acids in length and has a potential glycosylation site at residue N572, and potential phosphorylation sites at residues S15, R98, S113, K119, T150, S249, S259, S382, S308, T526, and S556. As shown in FIGS. 2A and 2B, MEND1 has chemical and structural homology with MEN1 (GI 1945387; SEQ ID NO:6), and they share 76% identity. Northern analysis which shows the expression of MEND1 in sequences from 48 different cDNA libraries (FIGS. 3A, 3B and 3C). MEND1 sequence was represented in 51 Incyte clones from 39 different libraries, 22 of which were cancer associated; and in 27 dbEST sequences from 10 different libraries, 2 of which were cancerous. Since at least 50% of the libraries with MEND1 sequence were from cells or tissues which are immortalized or cancerous, expression of MEND1 or its mutated variants appears to be upregulated in the cancerous state. Further analysis of aligned sequences revealed a mutation at nucleotide 1989 in the 3' non-coding region of the MEND1 cDNA. A cytosine was present at position 1989 in 2 sequences: Incyte Clone 1577445 (LNODNOT03), isolated from a patient with lung cancer, and Incyte Clone 1845962 (COLNNOT09) isolated from a patient with adenocarcinoma of the colon. Sequences definitely lacking this cytosine were Incyte Clone 1313372, isolated from a patient with transition cell carcinoma of the bladder Incyte Clone and 1450878 isolated from a patient with squamous cell carcinoma of the penis, and NCBI sequences g879120 and g907832, isolated from normalized brain library.

The invention also encompasses MEND1 variants which retain the biological or other functional activity of MEND1. A preferred MEND1 variant is one having at least 80%, and more preferably 90%, amino acid sequence identity to the MEND1 amino acid sequence (SEQ ID NO:1). A most preferred MEND1 variant is one having at least 95% amino acid sequence identity to SEQ ID NO:1.

The invention also encompasses polynucleotides which encode MEND1. Accordingly, any nucleic acid sequence which encodes the amino acid sequence of MEND1 can be used to produce recombinant molecules which express MEND1. In a particular embodiment, the invention encompasses the polynucleotide comprising the nucleic acid sequence of SEQ ID NO:2 as shown in FIGS. 1A, 1B, 1C, 1D and 1E.

It will be appreciated by those skilled in the art that as a result of the degeneracy of the genetic code, a multitude of nucleotide sequences encoding MEND1, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring MEND1, and all such variations are to be considered as being specifically disclosed.

Although nucleotide sequences which encode MEND1 and its variants are preferably capable of hybridizing to the nucleotide sequence of the naturally occurring MEND1 under appropriately selected conditions of stringency, it may be advantageous to produce nucleotide sequences encoding MEND1 or its derivatives possessing a substantially different codon usage. Codons may be selected to increase the rate at which expression of the peptide occurs in a particular prokaryotic or eukaryotic host in accordance with the frequency with which particular codons are utilized by the host.

Other reasons for substantially altering the nucleotide sequence encoding MEND1 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode MEND1 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding MEND1 or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507– 511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by Gibco/BRL (Gaithersburg, Md.). Preferably, the process is automated with machines such as the MICROLAB 2200 (Hamilton, Reno, Nev.), Peltier thermal cycler (PTC200; MJ Research, Watertown, Mass.) and the ABI Catalyst and 373 and 377 DNA Sequencers (Perkin Elmer).

The nucleic acid sequences encoding MEND1 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:1 11–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode MEND1 may be used in recombinant DNA molecules to direct expression of MEND1, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express MEND1.

As will be understood by those of skill in the art, it may be advantageous to produce MEND1 encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter MEND1 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding MEND1 may be ligated to a heterologous sequence to encode a fusion protein. For example, to screen peptide libraries for inhibitors of MEND1 activity, it may be useful to encode a chimeric MEND1 protein that can be recognized by a commercially available antibody. A fusion protein may also be engineered to contain a cleavage site located between the MEND1 encoding sequence and the heterologous protein sequence, so that MEND1 may be cleaved and purified away from the heterologous moiety.

In another embodiment, sequences encoding MEND1 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of MEND1, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of MEND1, or any part thereof, may be altered during direct synthesis and/or combined using chemical methods with sequences from other proteins, or any part thereof, to produce a variant polypeptide.

In order to express a biologically active MEND1, the nucleotide sequences encoding MEND1 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding MEND1 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding MEND1. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding MEND1, vectors based on SV40 or EBV may be used with an appropriate selectable marker.

In bacterial systems, a number of expression vectors may be selected depending upon the use intended for MEND1. For example, when large quantities of MEND1 are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding MEND1 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding MEND1 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express MEND1. For example, in one such system, *Autographa californica* nuclear polyhedrosis virus (AcNPV) is used as a vector to express foreign genes in *Spodoptera frugiperda* cells or in Trichoplusia larvae. The sequences encoding MEND1 may be cloned into a non-essential region of the virus, such as the polyhedrin gene, and placed under control of the polyhedrin promoter. Successful insertion of MEND1 will render the polyhedrin gene inactive and produce recombinant virus lacking coat protein. The recombinant viruses may then be used to infect, for example, S. frugiperda cells or Trichoplusia larvae in which MEND1 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding MEND1 may be ligated into an adenovirus transcription/translation complex consisting of the late promoter and tripartite leader sequence. Insertion in a non-essential E1 or E3 region of the viral genome may be used to obtain a viable virus which is capable of expressing MEND1 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding MEND1. Such signals include the ATG initiation codon and adjacent sequences. In cases where sequences encoding MEND1, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express MEND1 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic, or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14), and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding MEND1 is inserted within a marker gene sequence, transformed cells containing sequences encoding MEND1 can be identified by the absence of marker gene function. Alternatively, a marker gene can be placed in tandem with a sequence encoding MEND1 under the control of a single promoter. Expression of the marker gene in response to induction or selection usually indicates expression of the tandem gene as well.

Alternatively, host cells which contain the nucleic acid sequence encoding MEND1 and express MEND1 may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding MEND1 can be detected by DNA—DNA or DNA-RNA hybridization or amplification using probes or fragments or fragments of polynucleotides encoding MEND1. Nucleic acid amplification based assays involve the use of oligonucleotides or oligomers based on the sequences encoding MEND1 to detect transformants containing DNA or RNA encoding MEND1.

A variety of protocols for detecting and measuring the expression of MEND1, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on MEND1 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding MEND1 include oligolabeling, nick translation, end-labeling or PCR amplification using a labeled nucleotide. Alternatively, the sequences encoding MEND1, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding MEND1 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode MEND1 may be designed to contain signal sequences which direct secretion of MEND1 through a prokaryotic or eukaryotic cell membrane. Other constructions may be used to join sequences encoding MEND1 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and MEND1 may be used to facilitate purification. One such expression vector provides for expression of a fusion protein containing MEND1 and a nucleic acid encoding 6 histidine residues preceding a thioredoxin or an enterokinase cleavage site. The histidine residues facilitate purification on IMIAC (immobilized metal ion affinity chromatography), as described in Porath, J. et al. (1992, Prot. Exp. Purif. 3: 263–281), while the enterokinase cleavage site provides a means for purifying MEND1 from the fusion protein. A discussion of vectors which contain fusion proteins is provided in Kroll, D. J. et al. (1993; DNA Cell Biol. 12:441–453).

In addition to recombinant production, fragments of MEND1 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of MEND1 may be chemically synthesized separately and combined using chemical methods to produce the full length molecule.

THERAPEUTICS

Chemical and structural homology exits among MEND1 and MEN1 (GI 1945387). In addition, MEND1 is expressed in cDNA libraries made from bladder, brain, colon, kidney, liver, lymph node, pancreas, prostate, aortic smooth muscle and small intestine tissues, and in HNT2 teratocarcinoma and AZT-stimulated THP1 cells. Sixteen out of 20 tissues were removed from patients having surgery for cancers including adenocarcinoma, astrocytoma, hepatoma, squamous cell carcinoma, and transitional cell carcinoma. Therefore, MEND1 appears to play a role in multiple endocrine neoplasia when one or both normal genetic copies of MEND1 are mutated and no longer able to suppress tumorigenesis.

Therefore, in one embodiment, MEND1 or a fragment or derivative thereof may be administered to the cells of a subject to treat cancers including adenocarcinoma, leukemia, lymphoma, melanoma, multiple endocrine neoplasia, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing MEND1, or a fragment or a derivative thereof, may also be administered to the cells of a subject to treat the cancers listed above.

In another embodiment, a human artificial chromosome containing the polynucleotide sequence encoding MEND1 may be administered to the cells of a subject to treat the cancers listed above.

In other embodiments, the protein or vectors of the present invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of MEND1 may be produced using methods which are generally known in the art. In particular, purified MEND1 may be used to produce antibodies or to screen libraries of pharmaceutical agents to identify those which specifically bind MEND1.

Antibodies to MEND1 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with MEND1 or any fragment or oligopeptide thereof which has immunogenic properties.

Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to MEND1 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of MEND1 amino acids may be fused with those of another protein such as keyhole limpet hemocyanin and antibody produced against the chimeric molecule.

Monoclonal antibodies to MEND1 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce MEND1 encoding-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for MEND1 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MEND1 and its specific antibody. A two-site, monoclonal-based immunoassay utilizing monoclonal antibodies reactive to two non-interfering MEND1 epitopes is preferred, but a competitive binding assay may also be employed (Maddox, supra).

In another embodiment of the invention, the polynucleotides encoding MEND1, or any fragment or complement thereof, may be used for therapeutic purposes. In one aspect, the complement of the polynucleotide encoding MEND1 may be used in situations in which it would be desirable to block the transcription of the mRNA. In particular, cells may be transformed with sequences complementary to polynucleotides encoding MEND1. Thus, complementary molecules or fragments may be used to modulate MEND1 activity, or to achieve regulation of gene function. Such technology is now well known in the art, and sense or antisense oligonucleotides or larger fragments, can be designed from various locations along the coding or control regions of sequences encoding MEND1.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding MEND1. These techniques are described both in Sambrook et al. (supra) and in Ausubel et al. (supra).

Genes encoding MEND1 can be turned off by transforming a cell or tissue with expression vectors which express high levels of a polynucleotide or fragment thereof which encodes MEND1. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5'0 or regulatory regions of the gene encoding MEND1 (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding MEND1.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MEND1. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of MEND1, antibodies to MEND1, mimetics, agonists, antagonists, or inhibitors of MEND1. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of MEND1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example MEND1 or fragments thereof, antibodies of MEND1, agonists, antagonists or inhibitors of MEND1, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind MEND1 may be used for the diagnosis of conditions or diseases characterized by expression of MEND1, or in assays to monitor patients being treated with MEND1, agonists, antagonists or inhibitors. The antibodies useful for diagnostic purposes may be prepared in the same manner as those described above for therapeutics. Diagnostic assays for MEND1 include methods which utilize the antibody and a label to detect MEND1 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring MEND1 are known in the art and provide a basis for diagnosing altered or abnormal levels of MEND1expression. Normal or standard values for MEND1 expression are established by combining body fluids or cell extracts taken from normal mammalian subjects, preferably human, with antibody to MEND1 under conditions suitable for complex formation. The amount of standard complex formation may be quantified by various methods, preferably by photometric means. Quantities of MEND1 expressed in subject, samples from biopsied tissues are compared with the standard values. Deviation between standard and subject values establishes the parameters for diagnosing disease.

In another embodiment of the invention, the polynucleotides encoding MEND1 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of MEND1 may be correlated with disease. The diagnostic assay may be used to distinguish between absence, presence, and excess expression of MEND1, and to monitor regulation of MEND1 levels during therapeutic intervention.

In one aspect, hybridization with PCR probes which are capable of detecting polynucleotide sequences, including genomic sequences, encoding MEND1 or closely related molecules, may be used to identify nucleic acid sequences which encode MEND1. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding MEND1, alleles, or related sequences.

Probes may also be used for the detection of related sequences, and should preferably contain at least 50% of the nucleotides from any of the MEND1 encoding sequences.

The hybridization probes of the subject invention may be DNA or RNA and derived from the nucleotide sequence of SEQ ID NO:2 or from genomic sequence including promoter, enhancer elements, and introns of the naturally occurring MEND1.

Means for producing specific hybridization probes for DNAs encoding MEND1 include the cloning of nucleic acid sequences encoding MEND1 or MEND1 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding MEND1 may be used for the diagnosis of multiple endocrine neoplasia. The polynucleotide sequences encoding MEND1 may be used in Southern or northern analysis, dot blot, or other membrane-based technologies; in PCR technologies; or in dipstick, pin, ELISA assays or microarrays utilizing fluids or tissues from patient biopsies to detect altered MEND1 expression. Such qualitative or quantitative methods are well known in the art.

In a particular aspect, the nucleotide sequences encoding MEND1 may be useful in assays that detect activation or induction of various cancers, particularly those mentioned above. The nucleotide sequences encoding MEND1 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding MEND1 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of MEND1, a normal or standard profile for expression is established. This may be accomplished by combining body fluids or cell extracts taken from normal subjects, either animal or human, with a sequence, or a fragment thereof, which encodes MEND1, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MEND1 may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of MEND1 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212: 229–236). The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides derived from any of the polynucleotide sequences described herein may be used as probes in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs fixed to a solid support. Microarrays may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devises (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode MEND1 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding MEND1 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, MEND1, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between MEND1 and the agent being tested, may be measured.

Another technique for drug screening which may be used provides for high throughput screening of compounds having suitable binding affinity to the protein of interest as described in published PCT application WO84/03564. In this method, as applied to MEND1 large numbers of different small test compounds are synthesized on a solid substrate, such as plastic pins or some other surface. The test compounds are reacted with MEND1, or fragments thereof, and washed. Bound MEND1 is then detected by methods well known in the art. Purified MEND1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MEND1 specifically compete with a test compound for binding MEND1. In this manner, the antibodies can be used to detect the presence of any peptide which shares one or more antigenic determinants with MEND1.

In additional embodiments, the nucleotide sequences which encode MEND1 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRAINOT14 cDNA Library Construction

For purposes of example, the preparation of the BRAINOT14 cDNA library from which the 5' Incyte Clone 1596949 was isolated is described. Preparation of libraries in the LIFESEQ database and sequence analysis have varied only slightly over time and the gradual changes usually involve use of particular kits, plasmids, and machinery commercially available at a particular time.

BRAINOT14 was prepared within the past year from 1 microgram of polyA RNA isolated from nontumorous brain tissue removed from the left frontal lobe of a 40-year-old Caucasian female during excision of a cerebral meningeal lesion. Pathology for the associated tumor tissue indicated grade 4 gemistocytic astrocytoma. The patient presented with coma, epilepsy, incontinence of urine and stool, Type II diabetes, and paralysis. Patient history included chronic nephritis, and patient medications included Decadron (dexamethasone) and phenytoin sodium.

cDNA synthesis was initiated using a NotI-oligo d(T) primer. Double-stranded cDNA was blunted, ligated to EcoRI adaptors, and digested with NotI. cDNAs were fractionated on a SEPHAROSE CL4B column (Cat. #275105-01; Pharmacia), and those cDNAs exceeding 400 bp were ligated into pINCYI (Incyte Pharmaceuticals). The plasmid pINCY I was transformed into DH5a competent cells (Cat. #18258-012; Gibco/BRL).

II Isolation and Sequencing of cDNA Clones

Plasmid DNA was released from cells and purified using the R.E.A.L. PREP 96 plasmid kit (Catalog #26173; QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2200 (Hamilton, Reno, Nev.) in combination with Peltier thermal cyclers (PTC200 from MJ Research, Watertown, Mass.), and Applied Biosystems 377 DNA Sequencing Systems.

III Homology Searching of cDNA Clones and Their Deduced Proteins

After the reading frame was determined, the sequences of the Sequence Listing or their deduced amino acid sequences were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) Mol Evol 36:290–300; Altschul et al. (1990) J Mol Biol 215:403–410)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology. The relevant database for a particular match was reported as GIxxx±p (where xxx is pri, rod, etc and if present, p=peptide). The product score is calculated as follows: the % nucleotide or amino acid identity [between the query and reference sequences] in BLAST is multiplied by the % maximum possible BLAST score [based on the lengths of query and reference sequences] and then divided by 100. Where an Incyte Clone was homologous to several sequences, up to five matches were provided with their relevant scores. In an analogy to the hybridization procedures used in the laboratory, the electronic stringency for an exact match was set at 70, and the conservative lower limit for an exact match was set at approximately 40 (with 1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques use BLAST (Altschul (1993 and 1990) supra) to search for identical or related molecules in nucleotide databases such as the GenBank or the LIFESEQ database (FIGS. 3A, 3B and 3C). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding MEND1 occurs. Abundance and percent abundance are also reported. Abundance directly reflects the number of times a particular transcript is represented in a cDNA library, and percent abundance is abundance divided by the total number of sequences examined in the cDNA library.

V Extension of MEND1 Encoding Polynucleotides

The nucleic acid sequence of the Incyte Clone 1596949 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

| Step 1  | 94° C. for 1 min (initial denaturation) |
|---------|----------------------------------------|
| Step 2  | 65° C. for 1 min                       |
| Step 3  | 68° C. for 6 min                       |
| Step 4  | 94° C. for 15 sec                      |
| Step 5  | 65° C. for 1 min                       |
| Step 6  | 68° C. for 7 min                       |
| Step 7  | Repeat step 4–6 for 15 additional cycles |
| Step 8  | 94° C. for 15 sec                      |
| Step 9  | 65° C. for 1 min                       |
| Step 10 | 68° C. for 7:15 min                    |
| Step 11 | Repeat step 8–10 for 12 cycles         |
| Step 12 | 72° C. for 8 min                       |
| Step 13 | 4° C. (and holding)                    |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μg T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec                          |
|--------|--------------------------------------------|
| Step 2 | 94° C. for 20 sec                          |
| Step 3 | 55° C. for 30 sec                          |
| Step 4 | 72° C. for 90 sec                          |
| Step 5 | Repeat steps 2–4 for an additional 29 cycles |
| Step 6 | 72° C. for 180 sec                         |
| Step 7 | 4° C. (and holding)                        |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 software (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, or the blots are exposed in a Phosphoimager cassette (Molecular Dynamics, Sunnyvale, Calif.), hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the MEND1 encoding sequence, or any part thereof, is used to decrease or inhibit expression of naturally occurring MEND1. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of MEND1, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MEND1 encoding transcript.

IX Expression of MEND1

Expression of MEND1 is accomplished by subcloning the cDNAs into appropriate vectors and transforming the vectors into host cells. In this case, the cloning vector is also used to express MEND1 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of MEND1 into the bacterial growth media which can be used directly in the following assay for activity.

X Demonstration of MEND1 Activity

A cell line from the ATCC is transformed with a mutant form of the MEN1 gene (Chandrasekharappa, supra). The presence of MEN1 in these knockout cells causes an increase in the mitotic index as compared to untransformed cells of that cell line. A second transformation of the knockout cell line with a vector expressing normal MEND1 reduces the mitotic index back toward the normal level.

XI Production of MEND1 Specific Antibodies

MEND1 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc.) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring MEND1 Using Specific Antibodies

Naturally occurring or recombinant MEND1 is substantially purified by immunoaffinity chromatography using antibodies specific for MEND1. An immunoaffinity column is constructed by covalently coupling MEND1 antibody to an activated chromatographic resin, such as CNBr-activated SEPHAROSE (Pharmacia & Upjohn). After the coupling, the resin is blocked and washed according to the manufacturer's instructions.

Media containing MEND1 is passed over the immunoaffinity column, and the column is washed under conditions that allow the preferential absorbance of MEND1 (e.g., high ionic strength buffers in the presence of detergent). The column is eluted under conditions that disrupt antibody/protein binding (eg, a buffer of pH 2–3 or a high concentration of a chaotrope, such as urea or thiocyanate ion), and MEND1 is collected.

XIII Identification of Molecules Which Interact with MEND1

MEND1 or biologically active fragments thereof are labeled with $^{125}$Bolton-Hunter reagent (Bolton et al. (1973) Biochem. J. 133: 529). Candidate molecules previously arrayed in the wells of a multi-well plate are incubated with the labeled MEND1, washed and any wells with labeled MEND1 complex are assayed. Data obtained using different concentrations of MEND1 are used to calculate values for the number, affinity, and association of MEND1 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEQ ID NO:1.

2. A composition comprising the polynucleotide of claim 1.

3. An isolated and purified polynucleotide consisting of SEQ ID NO:2.

4. A composition comprising the polynucleotide of claim 3.

5. A polynucleotide which is fully complementary to the polynucleotide of claim 1.

6. A composition comprising the polynucleotide of claim 5.

7. An expression vector containing the polynucleotide of claim 1.

8. A host cell containing the expression vector of claim 7.

9. A method for producing a polypeptide comprising the amino acid sequence of SEQ ID NO:1, the method comprising the steps of:

a) culturing the host cell of claim 8 under conditions suitable for the expression of the polypeptide; and b) recovering the polypeptide from the host cell culture.

* * * * *